United States Patent [19]

Benn et al.

[11] Patent Number: 4,876,047
[45] Date of Patent: Oct. 24, 1989

[54] PROCESS FOR PRODUCING SULPHONIC ACID

[75] Inventors: Gerald Benn; David Farrar, both of Bradford; Peter Flesher, Bingley, all of United Kingdom

[73] Assignee: Allied Colloids Limited, England

[21] Appl. No.: 136,428

[22] Filed: Dec. 17, 1987

Related U.S. Application Data

[63] Continuation of Ser. No. 901,968, Aug. 29, 1986, abandoned, which is a continuation of Ser. No. 758,728, Jul. 25, 1985, abandoned.

[30] Foreign Application Priority Data

Jul. 27, 1984 [GB] United Kingdom ............... 8419207

[51] Int. Cl.$^4$ ........................................... C07C 143/16
[52] U.S. Cl. ...................................... 562/41; 562/105
[58] Field of Search ........................... 260/513 N, 508

[56] References Cited

U.S. PATENT DOCUMENTS 4,034,001 7/1977 Miller et al. ................... 260/513 N

OTHER PUBLICATIONS

Roberts Basic Principles of Org. Chem., 1965, pp. 654, 655.

Primary Examiner—Alan Siegel
Attorney, Agent, or Firm—Ostrolenk, Faber, Gerb & Soffen

[57] ABSTRACT

2-acrylamido 2-methyl propane sulphonic acid and other acrylamido-alkane sulphonic acids are made by reacting a compound such as t-butanol, t-butyl acetate or t-butyl methyl ester with a sulphonating agent in the absence of water, and then with a nitrile and water.

12 Claims, No Drawings

PROCESS FOR PRODUCING SULPHONIC ACID

This is a continuation of application Ser. No. 901,968 filed on Aug. 29, 1986, now abandoned, which is a continuation of application Ser. No. 758,728, filed July 25, 1985, now abandoned.

Beta-acrylamido alkane sulphonic acids are widely used as starting material in the production of water-soluble anionic polymers for various uses, for example as dispersants and flocculants. A widely used monomer of this type is 2-acrylamido-2-methyl propane sulphonic acid (trademark—AMPS).

Such monomers are generally made by low temperature reaction of an olefin such as isobutylene with a nitrile such as acrylonitrile and concentrated sulphuric acid. Such as process is described in GB 1,341,104. It is stated that the sulphuric acid should be at least 98% concentrated or should be oleum containing up to 30% sulphur trioxide. It is stated that the process is conducted by mixing the nitrile with the sulphuric acid and then adding the isobutylene or by blending the three reagents simultaneously. Before the addition of the isobutylene, the mixture of nitrile and sulphuric acid is preferably maintained below 0° C.

Isobutylene is a gas that is difficult and very dangerous to handle. Many manufacturers do not have the facilities to produce or use the gas, and many local authorities are unwilling to allow the use of isobutylene. The known processes for making AMPS are therefore unsatisfactory. Similar problems arise when making other monomers that require the use of volatile and dangerous olefinic starting materials.

Another route to 2-acrylamido-2-methyl propane sulphonic acid that has been proposed is by reaction of an alpha-sulphonic acid-beta-hydroxy compound with acrylonitrile; the process is described in PCT Specification No. WO84/00165. However the starting compound at present still has to be formed from the alpha,-beta-unsaturated compound, as disclosed in PCT Application No. WO84/00031. AMPS would therefore still be produced from isobutylene.

There is therefore a serious need to devise a process for the manufacture of monomers such as AMPS and which avoids the need to utilise an olefine as a starting material.

In the invention, we make a compound Formula 1

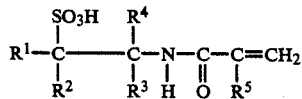

wherein $R_3$ and $R_4$ unsubstituted aryl and aralykyl having from 6 to 12 carbon atoms in total, $R_1$ and $R_2$ are selected from the same values as $R_3$ and $R_4$ and hydrogen, and $R_5$ is hydrogen or $C_{1-6}$ alkyl from a nitrile of the formula $H_2C=C(R^5)CN$ and a sulphonating agent by a process comprising reacting the nitrile, a compound of Formula II

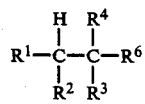

wherein $R^6$ provides a leaving group $R^6$ under acidic conditions with the sulphonating agent in the absence of water and with the nitrile and hydrolysing the product by reaction with added water.

Suitable leaving groups $R^6$ include a halogen atom, sulphate, aryloxy or aralkoxy (e.g., a triphenyl methoxy group) but is preferably acyloxy usually containing 1 to 8 carbon atoms or, more preferably, is hydroxy or alkoxy, usually containing 1 to 8 carbon atoms. Preferred groups $R^6$ are acetoxy or, preferably, hydroxy or methoxy.

The groups $R_1$ and $R_2$ are preferably hydrogen or lower alkyl (for instance $C_{1-4}$ alkyl), for example $R_1$ and $R_2$ may both be hydrogen or one of $R_1$ and $R_2$ may be hydrogen and the other may be methyl. $R_5$ is preferably hydrogen or methyl, usually hydrogen.

The groups $R_3$ and $R_4$ are preferably lower alkyl groups (for instance $C_{1-4}$ alkyl) and are usually both methyl groups, or one of the groups $R_3$ and $R_4$ is a methyl group and the other is a phenyl group.

Preferably $R_1$, $R_2$ and $R_5$ are hydrogen and $R_3$ and $R_4$ are methyl, the compound of Formula I then being AMPS.

A solvent is preferably included in the reaction mixture to make it less viscous and to absorb exotherm (especially when starting from the alcohol) and prevent charring. The solvent may comprise excess of the nitrile, which will also serve to drive the reaction towards the end products. However, there is a risk (especially when the sulphonating agent is strong oleum) of the nitrile charring if it is blended with the oleum in the absence of diluent and so preferably an additional solvent is used. The solvent may comprise non-polar solvent such as a chlorinated aliphatic hydrocarbon, for example dichloroethane or, preferably, methylene chloride, but preferably some or all of the solvent is a polar solvent, for example ethylene glycol dimethyl ether or, preferably an aliphatic carboxylic acid. Preferably acetic acid is used as solvent.

If $R^6$ is not OH, the compound of Formula II may be formed in situ by reaction with a compound where $R_6$ is OH with a derivatising agent that will introduce the group $R_6$ and that preferably will serve as the solvent in the reaction with the sulphonating agent and the acrylonitrile. For instance, if acetic or other carboxylic acid is included in the reaction mixture and a compound of Formula II wherein $R^6$ is OH is used, it appears that at least some of the end product of Formula I is formed as a result of the production within the reaction mixture of an intermediate which is the compound of Formula II wherein $R^6$ is acetoxy or other acyloxy group.

Instead of forming the ester by reaction within the mixture, it may alternatively be formed before introduction into the mixture, for instance by acylation of the tertiary alcohol. For instance the formate, propionate or butyrate or, preferably, acetate, may be formed by reaction of the tertiary alcohol with an appropriate acylating agent, for instance acetic anhydride, in the presence of a zinc chloride or other suitable catalyst.

It is particulary preferred to use compounds of Formula II which are ethers. If acetic acid is used as solvent, then alkyl acetate will be formed as a by-product and this provides a convenient way of removing the acetic acid from the reaction mixture.

It is preferred to react the compound of Formula II with the sulphonating agent in the substantial absence of water at a low temperature that is below 20° C. and then to react the resultant intermediate with the nitrile and water. The nitrile may be present throughout the process. Thus it is possible to obtain some suitable reaction by mixing the nitrile (generally in the presence of solvent) with the sulphonating agent and then adding the compound of Formula II at the low temperature and subsequently adding water to effect the hydrolysis. However yields are improved, and by product formation reduced by first mixing the compound of Formula II with the sulphonating agent at the low temperature and then adding the nitrile and water. Preferably the sulphonating agent is first diluted with solvent, the compound of Formula II is added, and subsequently the nitrile and water are added.

In GB 1,341,104, it was said to be essential to avoid combining the sulphuric acid with the olefin in the absence of the nitrile. Thus the preferred method of the invention involves an order of addition exactly opposite to the one specified in GB 1,341,104.

The reaction of the compound of Formula II with the sulphonating agent is preferably at a temperature of below 15° C. and generally below 0° C., for instance down to −15° C., generally −5° to −10° C. In general, it is best for the temperature to be as low as it can be without solidification of the reaction mixture and so choice of solvent influences the permissible temperature. The final reaction with the nitrile and the water is generally at an elevated temperature typically of above 30° C., preferably 60° to 80° C. If the temperature is up to 60° C., the reaction may need to be conducted for, e.g., 8 to 30 hours but at 60° to 90° C. duration of ½ to 8 hours (often 1 to 4 hours) may be sufficient, and shorter times may be sufficient at higher temperatures, e.g., up to 150° C.

Sufficient available water must be used to hydrolyse the nitrile to the amide. Some may be liberated during the overall process, e.g., by esterification of an alcohol of Formula II. Generally water must be added both to take up free $SO_3$ in the mixture, after the addition of sulphonating agent, and to hydrolyse the nitrile. The precise amount of water that is to be added must be determined by experimentation and will depend on, for instance, whether the compound of Formula II is generating hydroxyl groups and upon the concentration of oleum, if that is being used as the sulphonating agent. It is generally below 2, and preferably from 0.5 to 1.5, moles per mole of compound of Formula II although higher amounts, e.g., up to 3 moles, may be added in some instances.

The amount of sulphonating agent should be a molar (and preferably a stoichiometric) excess based on the compound of Formula II. It that compound is an ether or alcohol, it is generally necessary to include more than 2 moles, for instance 2.5 to 5 moles sulphonating agent per mole ether or alcohol but for other compounds of Formula II the amount of sulphonating agent typically can be from 1 to 3 moles, preferably 1.5 to 3 moles.

The molar ratio of the nitrile to the compound of Formula II should be above 1:1, preferably from 5:1 to 1.8:1, generally about 3:1 to 2:1.

The sulphonating agent preferably includes free sulphur trioxide and is preferably oleum. Best resullts appear to be achieved with concentrated oleums typically of 50 to 80% concentration (most preferably about 65% oleum). More dilute oleums can be used, e.g., down to 20% or more sometimes less, but the resultant increased amount of sulphuric makes it more difficult to recover the end product from the reaction mixture. Sulphuric acid by itself does not appear to be satisfactory, because the sulphonation must be conducted in the substantial absence of free water, and because of recovery problems. Other sulphonating agents that can be used include anhydrous reaction products of sulphur trioxide and organic compounds such as dioxane, dimethyl formamide or preferably, organic carboxylic acids. A preferred sulphonating agent is acetyl sulphate, $CH_3CO_2SO_3H$, formed by reaction of sulphur trioxide and glacial acetic acid at a low temperature.

It is known (see Calkins et al J.A.C.S. Vol 71 page 4144) that when tertiary butanol is reacted with sulphuric acid at low temperatures, the end product is almost entirely isobutane and is not isobutene. It appears that the process of the invention does not result in the formation of isobutene, as in GB 1,341,104, but instead involves some entirely different mechanism. In particular, the preferred processes go through an ether or ester of Formula II and this presumably cannot dehydrate to an olefine during the process. Even when starting from an alcohol, the reaction is best conducted in the presence of acetic acid and the formation of an ester, rather than an unsaturated compound, then appears to be an essential intermediate. Observation of the reaction mixture during the process does not appear to indicate the formation of an olefine as an intermediate.

The reaction of the sulphonating agent and the compound of Formula II is sometimes exothermic (for instance when the compound is an alcohol) in which event strong cooling must be applied during the reaction.

The desired end product of Formula I is generally obtained from the reaction mixture by crystallization. This may occur at an elevated reaction temperature or precipitation may be promoted by cooling and/or adding organic solvent.

The preferred process may be run continuously by continuous removal of the solid and liquid products, for example by centrifugation. The crystalline alkane sulphonic acid is usually washed. The liquid products may be distilled to recover, for instance excess acrylonitrile, and acetic acid or other solvent and unreacted compound of Formula II. These products can all be recycled for use in further reactions according to the invention. Sulphuric acid remaining from the sulphonation step may be recovered but is usually discarded.

The monomers formed by the process of the invention may be homopolymerised or, more usually, are copolymerised with a comonomer, for example, acrylamide or acrylic acid, to form an anionic polymer. The polymers are usually water soluble and may be used for various applications, their properties being dependent upon the comonomers and the reaction conditions. Examples of some uses are as dispersants, thickeners and flocculants.

The following are examples of the invention.

EXAMPLE 1

74 g of tertiary butanol, 320 g of glacial acetic acid and 172 g of methylene chloride were mixed together in a reaction vessel. The mixture was cooled to a temperature in the range −10° C. to −5° C. and then 248 g of 65% oleum was added slowly whilst stirring and cooling the mixture strongly to maintain the temperature at about 0° C. The resultant mixture was stirred for about 2 hours whilst keeping the temperature at between −5° and −10° C.

40 g of water and 106 g of acrylonitrile are then added to the reaction mixture whilst stirring. The mixture was heated to 60° C. at which temperature it was maintained for between 16 and 20 hours. To the product was added 600 ml acetone and 600 ml methylene chloride and the mixture was seeded with crystalline AMPS and cooled to −10° C. for about 2 hours. The crystalline AMPS product was filtered off and washed with acetic acid followed by acetone, and then dried at 75° to 80° C. The yield was 48% theoretical maximum.

EXAMPLE 2

58 g of tertiary butyl acetate, 160 g of glacial acetic acid and 86 g of methylene chloride were added to a reaction vessel and cooled to a temperature between −10° and −5° C. 62 g of 65% oleum were added to the reaction mixture whilst stirring and cooling gently to maintain the temperature at 0° C. The resultant mixture was allowed to warm to room temperature over a period of about 1 hour.

20 g of water and 53 g of acrylonitrile were added to the reaction mixture and the mixture was maintained at a temperature of 60° C. for 16 hours. AMPS crystallised without the further addition of organic solvent, whilst the temperature of the product mixture was at 60° C. The white crystalline product was filtered off from the product mixture and washed with acetic acid and methylene chloride. Further AMPS was obtained by diluting the filtrate with acetone and methylene chloride and cooling for a period of about half an hour at −10° C. to crystallise out further AMPS.

The yield of AMPS was 53.6 g (52% theoretical).

EXAMPLE 3

160 g of glacial acetic acid and 100 g methylene chloride were cooled at −10° C. in a stirred reaction vessel. 124 g of 65% oleum was added dropwise whilst maintaining the temperature below 0° C. 44gm methyl t-butyl ether was added over 45 minutes keeping the temperature below 0° C. After stirring for a further 30 minutes, 20gm water and 106gm acrylonitrile were added and the mixture heated at 65° C. for 16 hours. In order to aid crystallization and subsequent filtration, 300ml of a mixture of methylene dichloride, acetone and glacial acetic acid in equal volumes was added. The mixture was cooled to −10° C., the white crystalline product filtered off and washed with glacial acetic acid and acetone. The yield of AMPS was 74.0gm (72% theoretical).

EXAMPLE 4

160gm glacial acetic acid and 86 gm methylene chloride were mixed and cooled to −10° C. 44gm methyl t-butyl ether was added maintaining the temperature below 0° C. 124 gm of 65% oleum was added keeping the temperature below 0° C. After stirring for 1 hour at 0° C., the mixture was allowed to warm to room temperature (22° C.) before addition of 106gm acrylonitrile and 20gm water. The mixture was heated at 60° C. for 16 hours. After cooling to −10° C., 100mls methylene chloride and 100 mls acetone were added. The resulting white crystalline material was filtered and dried. The yield of AMPS was 46 gm (44% theoretical).

EXAMPLE 5

104.3 gm 65% oleum was added to 179.4 gm glacial acetic acid keeping the temperature at 10−15° C. The temperature of the mix was lowered to 0°−5° C. and 49.3 gm methyl t-butyl ether added dropwise. 59.4 gm acrylonitrile and 11.2 gm water were added keeping the temperature below 10° C. The mixture was heated at 80° C. for 2 hours, cooled to 10° C. and 200 gm glacial acetic acid added to aid filtration. The filtered white crystalline solid AMPS was reslurried with 200 gm acetone, filtered and dried at 60° C. Yield of AMPS =66.0 gm (57% theoretical).

We claim:

1. A process for making a compound of Formula I

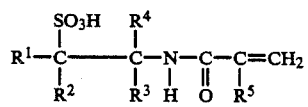

wherein $R_3$ and $R_4$ are independently selected from $C_{1-8}$ alkyl, substituted aryl, unsubstituted aryl and aralkyl having from 6 to 12 carbon atoms in total, $R_1$ and $R_2$ are selected from the same values as $R_3$ and $R_4$ and hydrogen, and $R_5$ is hydrogen or $C_{1-6}$ alkyl from a nitrile of formula $H_2C=C(R^5)CN$ where $R^5$ is hydrogen or $C_{1-6}$ alkyl and a sulphonating agent characterized in that the process comprises reacting below 20° C. a compound of Formula II

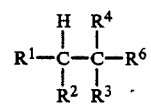

with the sulphonating agent in the substantial absence of water and with the nitrile and hydrolyzing the product by reaction 30° C. with added water to produce the compound of Formula I wherein $R^6$ selected from the group consisting of hydroxy, alkoxy, acyloxy, halogen, sulphate, aryloxy and aralkoxy.

2. A process according to claim 1 comprising mixing the compound of Formula II with the sulphonating agent in the absence of water and at a low temperature that is below 20° C. and then adding the nitrile and water and reacting the mixture to an elevated temperature of above 30° C.

3. A process according to claim 2 in which the low temperature is a temperature of −15° C. to 0° C. at which the mixture is liquid and the elevated temperature is 60° to 90° C.

4. A process according to claim 1 in which the sulphonating agent is selected from oleum and acetyl sulphate.

5. A process according to claim 1 in which the sulphonating agent is 50 to 80% oleum.

6. A process according to claim 1 in which $R^6$ is hydroxy, $C_{1-8}$ alkoxy or $C_{1-8}$ acyloxy.

7. A process according to claim 1 in which $R^6$ is hydroxy, methoxy or acetoxy.

8. A process according to claim 1 in which $R^1$, $R^2$ and $R^5$ are hydrogen and $R^3$ and $R^4$ are methyl.

9. A process according to claim 1 in which the reaction is conducted in the presence of a polar solvent.

10. A process according to claim 1 in which the reaction is conducted in the presence of acetic acid.

11. A process according to claim 1 in which the molar ratio of compound of Formula II:nitrile:added water is 1:2−3:0.5−1.5.

12. A process for making a compound of Formula I

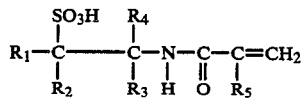

I wherein $R_3$ and $R_4$ are indpendently selected from $C_{1-8}$ alkyl, substituted aryl, unsubstituted aryl and aralkyl having from 6 to 12 carbon atoms in total, $R_1$ and $R_2$ are selected from the same values as $R_3$ and $R_4$ and hydrogen, and $R_5$ is hydrogen or $C_{1-6}$ alkyl from a nitrile of formula $H_2C=C(R_5)CN$ where $R_5$ is hydrogen or $C_{1-6}$ alkyl and a sulphonating agent characterized in that the process comprises reacting 20° C. a compound of Formula II

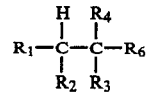

with 50–80% oleum in the substantial absence of water and with the nitrile and hydrolyzing the product by reaction 30° C. with added water to produce the compound of Formula I wherein $R_6$ selected from the group consisting of hydroxy, alkoxy, acyloxy, halogen, sulphate, aryloxy and aralkoxy.

* * * * *